(12) United States Patent
Ma et al.

(10) Patent No.: US 11,439,333 B2
(45) Date of Patent: Sep. 13, 2022

(54) BLOOD COLLECTION SYSTEM INCLUDING A BAFFLE

(71) Applicant: Becton, Dickinson and Company, Franklin Lakes, NJ (US)

(72) Inventors: Yiping Ma, Layton, UT (US); Joseph Spataro, Cottonwood Heights, UT (US); Huy Tran, Riverton, UT (US); Kathryn Willybiro, Park City, UT (US); Jonathan Karl Burkholz, Salt Lake City, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 220 days.

(21) Appl. No.: 16/741,923

(22) Filed: Jan. 14, 2020

(65) Prior Publication Data

US 2020/0229746 A1    Jul. 23, 2020

Related U.S. Application Data

(60) Provisional application No. 62/794,436, filed on Jan. 18, 2019.

(51) Int. Cl.
*A61B 5/15*    (2006.01)

(52) U.S. Cl.
CPC .... *A61B 5/150992* (2013.01); *A61B 5/15003* (2013.01); *A61B 5/150053* (2013.01); *A61B 5/150343* (2013.01)

(58) Field of Classification Search
CPC ...... A61B 5/1411; A61B 5/1473; A61M 1/02; A61M 1/3627; A61M 1/3626; A61M 1/631; A61M 2205/3331; A61M 2205/3334; A61M 39/0613; B01D 33/01; B01D 61/22

See application file for complete search history.

(56) References Cited

U.S. PATENT DOCUMENTS

| | | | |
|---|---|---|---|
| 2,594,621 A * | 4/1952 | Derrick | A61B 5/150389 600/577 |
| 3,757,771 A | 9/1973 | Ruegg et al. | |
| 4,492,634 A | 1/1985 | Villa-Real | |
| 5,055,198 A * | 10/1991 | Shettigar | A61M 1/3403 210/650 |
| 5,084,034 A | 1/1992 | Zanotti | |
| 5,265,621 A * | 11/1993 | Simpson | A61M 5/315 600/577 |
| 5,505,721 A | 4/1996 | Leach et al. | |
| 9,839,385 B2 | 12/2017 | Burkholz | |

(Continued)

FOREIGN PATENT DOCUMENTS

| | | |
|---|---|---|
| CN | 205072879 | 3/2016 |
| WO | 98/44970 | 10/1998 |

(Continued)

*Primary Examiner* — Patrick Fernandes
*Assistant Examiner* — S. P. L.
(74) *Attorney, Agent, or Firm* — Kirton McConkie; Whitney Blair; Kevin Stinger

(57) ABSTRACT

A blood sample collection system, may include a housing, the housing including a blood collection port; and a baffle chamber; a needle formed through the housing and into the blood collection port; and a baffle formed within the baffle chamber to counteract a vacuum within a blood collection tube when pierced by the needle.

12 Claims, 8 Drawing Sheets

(56) References Cited

U.S. PATENT DOCUMENTS

| | | | |
|---|---|---|---|
| 2003/0208160 A1* | 11/2003 | Crawford | A61B 5/15074 |
| | | | 604/164.08 |
| 2005/0281713 A1 | 12/2005 | Hampsch et al. | |
| 2006/0009713 A1* | 1/2006 | Flaherty | A61B 5/150213 |
| | | | 600/576 |
| 2012/0252709 A1 | 10/2012 | Felts et al. | |
| 2014/0042094 A1 | 2/2014 | Montagu et al. | |
| 2015/0005669 A1 | 1/2015 | Burkholz | |
| 2018/0264195 A1* | 9/2018 | Hopkins | A61M 5/31596 |

FOREIGN PATENT DOCUMENTS

| | | |
|---|---|---|
| WO | 01/43795 | 6/2001 |
| WO | 2005/011773 | 2/2005 |

* cited by examiner

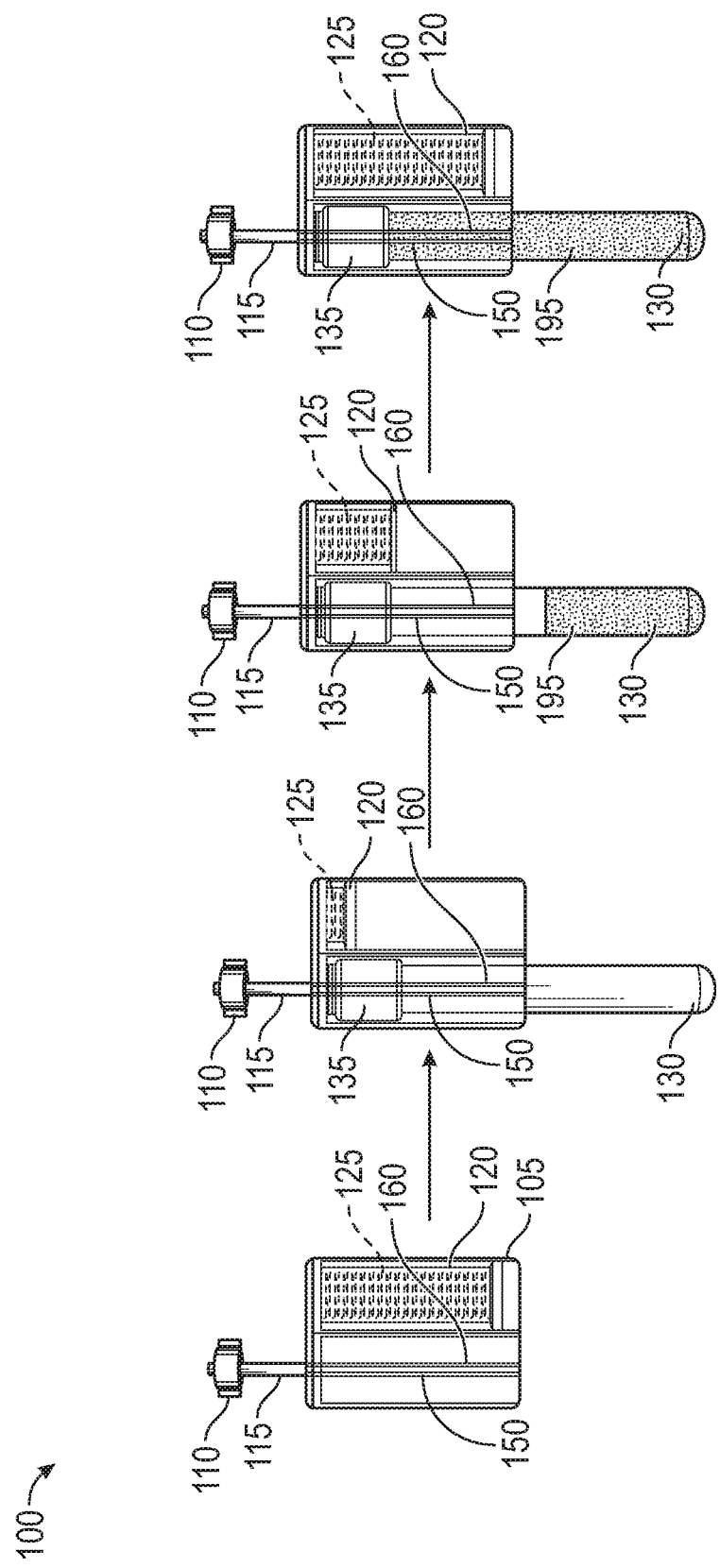

BLOOD COLLECTION SYSTEM INCLUDING A BAFFLE

RELATED APPLICATIONS

This application claims the benefit of U.S. Provisional Application No. 62/794,436, filed Jan. 18, 2019, and entitled SAMPLE COLLECTION TUBE, which is incorporated herein in its entirety.

BACKGROUND

Hemolysis is the rupturing of blood cells. When a blood cell undergoes hemolysis, the contents to the cells may be ripped out from within the cell wall. This results in the destruction of the cell itself as well as potentially destroying the ability to analyze the cells and other fluids received in, for example, a blood sample.

During a blood draw, a blood sample is received via an intravenous (IV) device such as a peripheral intravenous catheter (PIVC). The IV may allow a flow of blood to pass through the IV and into a blood collection tube. Some blood collection tubes may include a plastic or glass tube that has a vacuum formed therein and sealed using a rubber stopper. An example blood collection tube is a VACUTAINER® developed by Becton Dickinson, and Company.

However, during operation of the vacuum blood collection tubes, the negative pressure within the blood collection tube may apply a significant amount of force on the collected sample sufficient to cause hemolysis. The pressure may also be significant enough to cause a distal end of the catheter to fish-mouth, creating a smaller opening which increases the induced shear on the blood cells as they pass through the IV catheter placed within a patient's blood vessel.

The pressure induced by the vacuum blood collection tube is created by evacuating the collection tube by a known volume where the greater the volume evacuated results in a greater amount of negative pressure. By way of example, a 10 ml volume that is placed under vacuum may create a negative pressure of 600 mmHg within the blood collection tube.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to a blood sample collection system and related systems and methods. In some embodiments, the blood sample collection system provides for the collection of a blood sample without degradation of the that sample even when a vacutainer-type blood collection tube is used. Additionally, the blood sample collection system may include a compressed saline flush tube that interfaces with the blood sample collection system after the blood sample has been taken at the vacutainer-type blood collection tube and used to flush an IV fluidically coupled to the blood sample collection system.

In some embodiments, the blood sample collection system may include a housing, the housing may include a blood collection port; and a baffle chamber; a needle formed through the housing and into the blood collection port; and a baffle formed within the baffle chamber to counteract a vacuum within a blood collection tube when pierced by the needle. The housing may include two needles that are placed to pierce a rubber membrane of the blood collection tube and the compressed saline flush tube. During operation, the baffle may reduce the sheer forces placed on a sample of blood during the blood draw process by effectively reducing the vacuum pressures within the blood collection sample. The volume of the baffle may be reduced initially when the vacutainer-type blood collection tube is introduced at the blood collection port. As the sample of blood is collected into the blood collection tube, the negative pressure created by the vacuum within the tube drops allowing the baffle to recover due to a spring placed within the baffle or an elastomeric material property of the baffle itself. The baffle may continue to recover until the baffle is restored to its fully expanded state.

The blood sample collection system also includes the saline flush tube. The saline flush tube may be introduced at the blood collection port so that saline may be forced through the catheter to clear the catheter of blood or other fluids. In order to force the saline out of the saline flush tube, the saline flush tube may include one of a plunger, compressed air, or a spring system that forces the saline out of the saline flush tube.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4 is a flow diagram illustrating an operation of a blood sample collection system according to an embodiment of the present disclosure;

DESCRIPTION OF EMBODIMENTS

Figure 1:
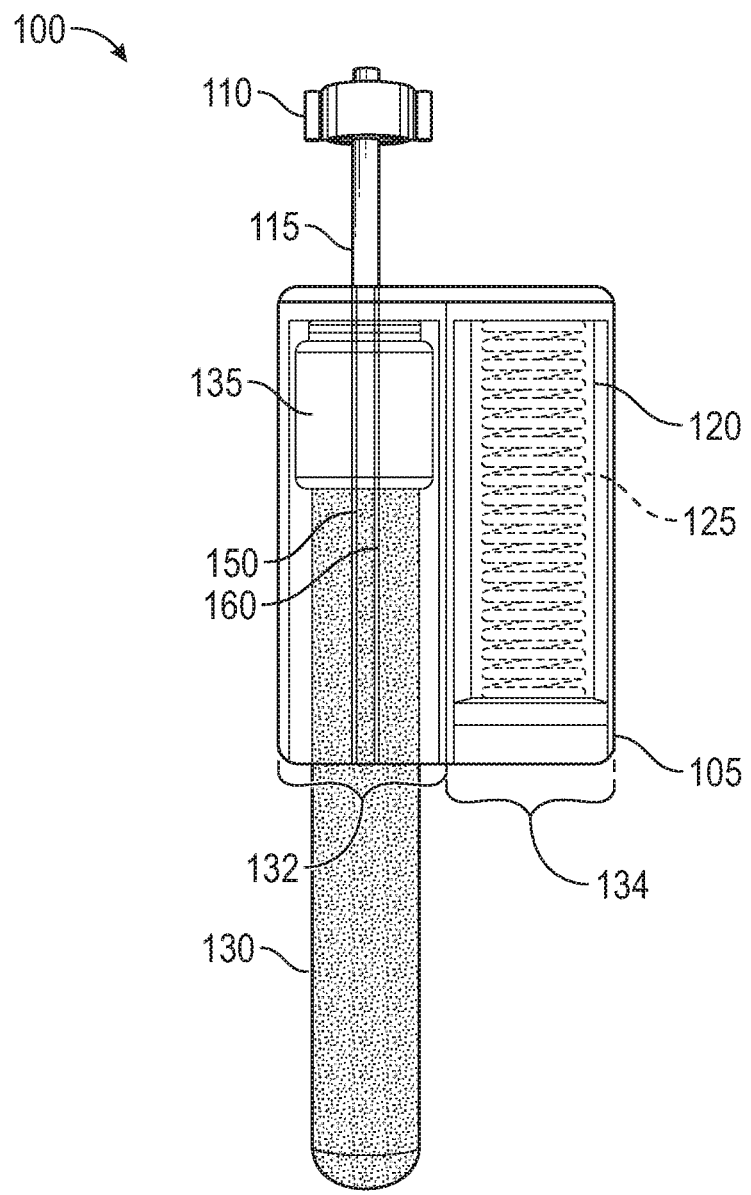
FIG. 1 is a side view of a blood collection system according to an embodiment of the present disclosure.

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

FIG. 1 is a side view of a blood collection system 100 according to an embodiment of the present disclosure. The blood collection system 100 may include a housing 105. The housing 105 may include a blood collection port 132 to receive a blood collection tube 130 therein. The housing 105 may further include a baffle chamber 134. The baffle chamber 134 may house a baffle 120 and a baffle spring 125 therein. These will now be described in more detail.

The housing 105 may be made of any resilient material used to rigidly house the blood collection tube 130 and baffle 120 as described herein. The material used to form the housing 105, in an embodiment may be made of a clear or translucent material to allow a clinician or other health care provider (HCP) to view, at least, the blood collection tube 130 placed within the blood collection port 132 during operation.

The blood collection port 132 may include a collection needle 150. The collection needle 150 may be fluidically coupled to a hub 110 and a hub lead 115. During operation, the collection needle 150 may be inserted into the blood collection tube 130 piercing a rubber membrane formed into a cap 135 formed on the blood collection tube 130. As such, during operation, the blood collection tube 130 may be inserted into the blood collection port 132 and interfaced with the collection needle 150 so as to fluidically couple the interior of the blood collection tube 130 with a blood vessel within a patient's body.

The hub 110 may be formed so as to interface with an intravenous (IV) catheter. In an embodiment, the hub 110 may include threads or other types of coupling devices used to couple the hub 110 to a lead on an IV catheter. This coupling allows for the blood collection system 100 to be selectively coupled and uncoupled from the IV catheter according to the embodiments of the present disclosure. In an embodiment, the hub 110 may be fluidically coupled to the collection needle 150 by a hub lead 115. The hub lead 115 may be made of a plastic in an embodiment.

As described, the baffle chamber 134 may house a baffle 120. The baffle 120 may be made of any material that is capable of holding an amount of gas therein. In an embodiment, the baffle 120 is made of a pliable material that may be collapsed and expanded during operation of the blood collection system 100 as described herein. In an embodiment, the baffle 120 may be made of a pliable plastic, a pliable rubber, an airtight cloth, among other deformable and pliable material.

In an embodiment, the baffle chamber 134 and baffle 120 may include a spring 125. The spring 125 may be placed within the baffle 120 and biased so that the baffle 120 is in an expanded state as shown in FIG. 1. The spring 125 may be placed against a wall of the housing 105 and an internal distal end of the baffle 120.

The housing 105 may also include a baffle needle 160. In an embodiment, the baffle needle 160 may be atmospherically coupled to the interior of the baffle 120 such that an amount of gas maintained within the baffle 120 may pass through the baffle needle 160 during operation of the blood collection system 100. The baffle needle 160 may be atmospherically coupled to the interior of the baffle 120 via, in an embodiment, a baffle conduit (not shown). The baffle conduit may be formed within the housing 105 itself in an embodiment. In another embodiment, the baffle conduit may be a tube that atmospherically couples the interior of the baffle 120 to the baffle needle 160.

During operation of the blood collection system 100, a blood collection tube 130 may be introduced into the blood collection port 132. As described herein, the cap 135 of the blood collection tube 130 may include a rubber membrane that is pierced by the baffle needle 160 and collection needle 150 upon insertion of the blood collection tube 130. The collection needle 150 may communicatively couple the interior of the blood collection tube 130 with an IV catheter placed within a blood vessel of a patient. Concurrently, the baffle needle 160 may be atmospherically couple the interior of the blood collection tube 130 with the gases present within the baffle 120. Because of the vacuum previously present within the blood collection tube 130, the baffle 120 may collapse due to the gases within the baffle 120 being displaced into the interior of the blood collection tube 130.

The collapsing of the baffle 120 may overcome the mechanical forces of the spring 125 therein. In an embodiment, the spring forces of the spring 125 may be such that the change in atmospheric pressures between the interior of the blood collection tube 130 and the interior of the baffle 120 may initially overcome those spring forces. As the blood is drawn into the blood collection tube 130 via the IV catheter from the patient's blood vessel, the blood may replace an amount of gas present in the blood collection tube 130 originating from the interior of the baffle 120. These gases may be returned to the interior of the baffle 120 as blood is accumulated into the interior of the blood collection tube 130. The removal of gases from within the blood collection tube 130 and into the baffle 120 may allow the spring 125 to expand the baffle 120 eventually to its original expanded state as shown in FIG. 1. This final state is depicted in FIG. 1 with the blood collection tube 130 having displaced all or most of the gases provided to it by the baffle 120 back into the baffle 120 and the spring 125 expanding the baffle 120 to its original or near original state.

During operation of the blood collection system 100, any number of blood collection tubes 130 may be inserted, sequentially, into the blood collection port 132 so that multiple blood samples may be retrieved at the blood collection system 100. Upon each insertion of a blood collection tube 130, the vacuum within the blood collection tube 130 may collapse the baffle 120 and re-expand the baffle 120 as described herein. The operation of the baffle 120 provides a dampening mechanism that slows down the speed of the blood sample passing from the patient's blood vessel, through the hub 110 and hub lead 115, through the collection needle 150, and into the interior of the blood collection tube 130. This reduction in speed of the blood through these fluidic channels prevents a sheering force placed on the blood sample and its components such as the blood cells. This prevents damage from occurring in the sample and the obtaining of a usable sample throughout the blood draw. Additionally, the reduction in speed of the flow of blood through the fluidic channels described is a result of the conveyance of the gases within the baffle 120 into the blood collection tube 130 thereby reducing the atmospheric pressure of the created by the vacuum within the blood collection tube 130 and allowing the blood to still pass into the blood collection tube 130. This reduction in pressure also reduces the chance or prevents the occurrence of a distal end of an IV catheter from collapsing on itself thereby concurrently preventing hemolysis and stoppage of blood through the catheter and blood collection system 100. With lower vacuum pressures present in the system blood collection system, the pressure gradient and velocity of the blood flow into the blood collection tube 130 are decreased. The result is a decrease in shear stress on the blood cells collected thereby reducing blood cell hemolysis.

The blood collection system 100, in some embodiments, may also include a saline flush tube (not shown). In this embodiment, after the blood collection tube 130 has been removed, the saline flush tube may be coupled to the housing 105 at the blood collection port 132. In order to facilitate the passage of the saline in the saline flush tube through the housing 105 and into the IV catheter coupled to the housing 105 via the hub 110, the saline flush tube may include a compression force mechanism that pushes the saline out of the saline flush tube. The compression force mechanism, in an embodiment, may be an amount of compressed air within the saline flush tube. In this embodiment, the saline flush tube may be introduced into the blood collection tube 130 causing a rubber membrane in a cap of the saline flush tube to be punctured by the collection needle 150. In this embodiment, the saline flush tube may be made to be upright with the compressed air in the saline flush tube at a distal end of the saline flush tube. This compressed air may then force the saline through the collection needle 150 and into the IV thereby clearing the IV of any blood that may, for example clot therein.

In another embodiment, the compression force mechanism may be a plunger having a plunger arm and plunger head. During operation of the saline flush tube in this embodiment, a rubber membrane present in the cap of the saline flush tube may be punctured by the collection needle 150. The clinician may then apply force to the plunger arm which then applies that force to a plunger head. The plunger head may then place a force on the saline within the saline flush tube causing the saline to pass through the IV catheter thereby clearing the IV of any blood that may, for example clot therein.

In another embodiment, the compression force mechanism may be a spring that is mechanically coupled to a plunger head within the saline flush tube. In this embodiment, the spring within the saline flush tube may be biased to force the plunger head towards a cap of the saline flush tube. When a rubber membrane of the cap is punctured by the collection needle 150, the saline is forced into the IV catheter coupled to the housing 105 of the blood collection system 100 thereby clearing the IV of any blood that may, for example clot therein.

In an embodiment, the baffle conduit (not shown) may include a filter (not shown) formed therein. In this embodiment, the filter may prevent a liquid such as the saline in the saline flush tube or a blood sample within the blood collection tube 130 from entering the interior of the baffle 120. In this embodiment, the filter may be a one-time filter that, upon contact of the filter with a liquid, the filter is sealed. In an embodiment, the filter may be any barrier that is permeable to gas but impermeable to a liquid in order to prevent contaminates from entering into the baffle 120.

Figure 2:
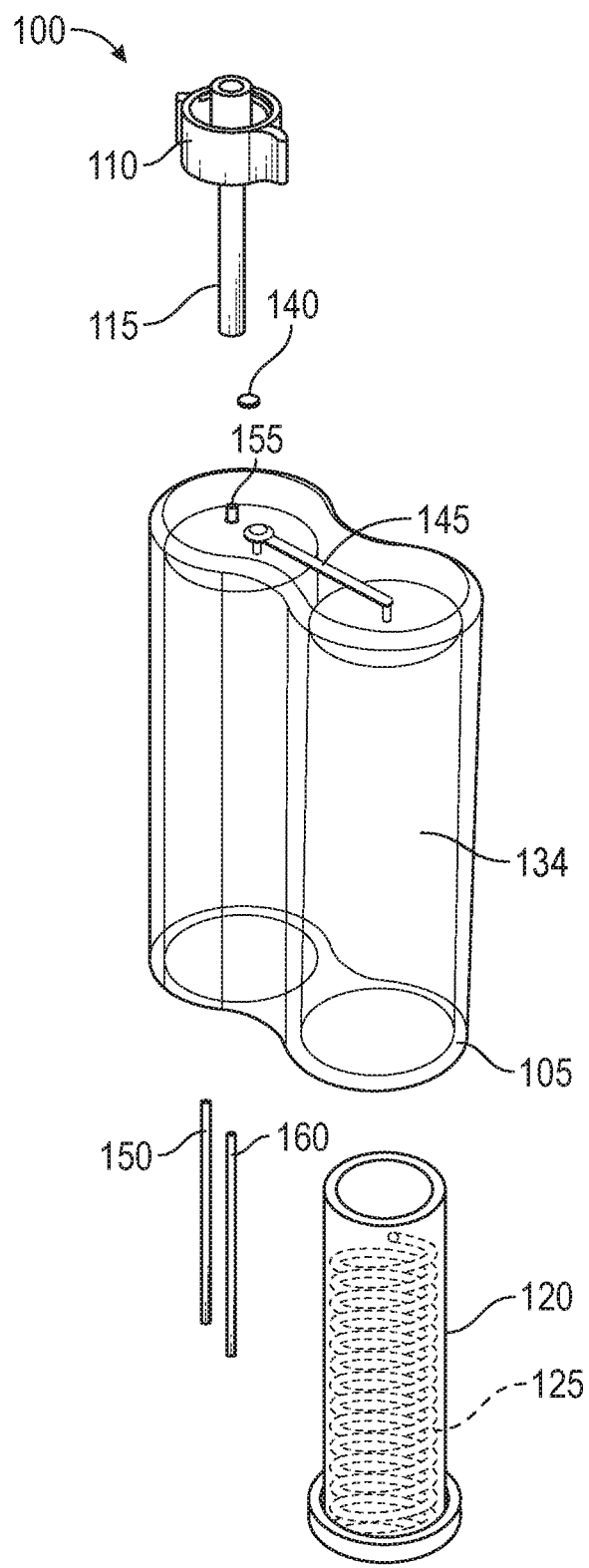
FIG. 2 is a perspective, exploded view of a blood collection system according to an embodiment of the present disclosure.

FIG. 2 is a perspective, exploded view of a blood collection system 100 according to an embodiment of the present disclosure. The exploded view shows the elements of the blood collection system 100 relative to each other so that these elements may be viewed outside of the housing 105.

As described, the blood collection system 100 includes a housing 105. The housing 105 may include a blood collection port 132 to receive a blood collection tube 130 therein. The housing 105 may further include, when assembled, a baffle chamber 134. The baffle chamber 134 may house a baffle 120 and a baffle spring 125 therein.

The baffle 120 may house a spring 125 therein that biases a distal end of the baffle 120 away from in internal surface of the housing 105. As seen in FIG. 2, the interior of the baffle 120 may be atmospherically coupled to a baffle conduit 145. The baffle conduit 145 may be formed within a portion of the housing 105 such that the baffle conduit 145 may also be in atmospheric communication with a baffle needle 160. As described herein, the baffle needle 160 and baffle conduit 145 may atmospherically coupled an interior of a blood collection tube (not shown) with the interior of the baffle 120 to accomplish the methods described herein.

In an embodiment, the baffle conduit 145 may further include a filter 140. The filter 140 may be placed anywhere within the atmospheric channel formed by the baffle needle 160, the baffle conduit 145, and the interior of the baffle 120. In a specific embodiment, the filter 140 is placed at a location where the baffle needle 160 is coupled to the housing 105 at the baffle conduit 145. As described herein, the filter 140 be any barrier that is permeable to gas but impermeable to a liquid in order to prevent contaminates from entering into the baffle 120. This may include, for example, a one-time valve that closes once a liquid such as saline or blood comes in contact with the one-time valve. In a specific example, when a compressed saline flush tube is introduced at the blood collection port 132, the saline may make contact with the filter 140 when the saline is compressed through the collection needle 150 and baffle needle 160 sealing the baffle 120 from receiving saline therein and reserving the saline for flushing the IV catheter as described herein.

The assembly of the blood collection system 100 may include operatively coupling the hub 110 and hub lead 115 through the housing 105 and with a collection needle 150. The assembly may include operatively coupling the baffle needle 160 to the baffle conduit 145 and placing the spring 125 and baffle 120 into the baffle chamber 134.

Figure 3A:
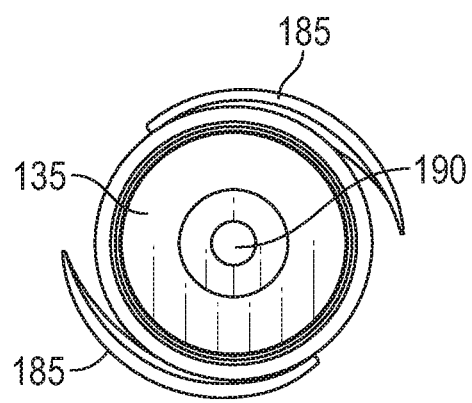
FIG. 3A is a top view of a blood collection tube according to an embodiment of the present disclosure.
Figure 3B:
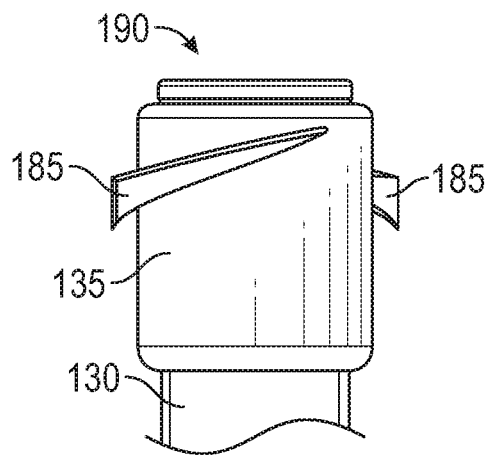
FIG. 3B is a side view of a cap of a blood collection tube according to an embodiment of the present disclosure.
Figure 3C:
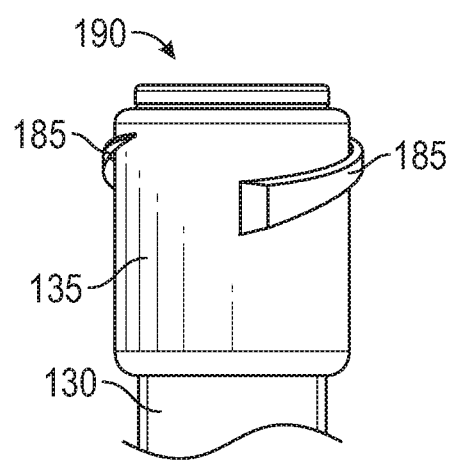
FIG. 3C is a side view of a cap of a blood collection tube according to an embodiment of the present disclosure.

FIG. 3A is a top view of a blood collection tube 130 according to an embodiment of the present disclosure. Additionally, FIG. 3B is a side view of a cap 135 of a blood collection tube 130 according to an embodiment of the present disclosure. Still further, FIG. 3C is a side view of a cap 135 of a blood collection tube 130 according to an embodiment of the present disclosure. FIGS. 3A, 3B, and 3C show that the cap 135 of the blood collection tube 130, in an embodiment, includes a rubber membrane 190. As described herein, the rubber membrane 190 may be pierced by a collection needle and a baffle needle upon insertion of the blood collection tube 130 into a blood collection port formed within the housing of the blood collection system. The rubber membrane 190 may be formed to seal the blood collection tube 130 when pierce by the collection needle and baffle needle. Additionally, the rubber membrane 190 may be formed to also seal the blood collection tube 130 when the blood collection tube 130 is removed from the blood collection port and the collection needle and baffle needle are no longer in fluid communication with the interior of the blood collection tube 130.

The cap 135 as shown in FIGS. 3A, 3B, and 3C also shows a number of threads 185 formed on an exterior surface of the cap 135. In an embodiment, the threads 185 may allow the clinician to semi-permanently couple the blood collection tube 130 at the blood collection port by pressing the blood collection tube 130 into the blood collection port and twisting the blood collection tube 130, in an example, clockwise. This twisting of the blood collection tube 130 into the blood collection port cause the threads 185 to mechanically engage with a complementary set of threads (not shown) formed within an interior surface of the blood collection port of the housing as described herein. In order to disengage the blood collection tube 130 from the housing, the clinician may turn the blood collection tube in a counterclockwise direction, for example, to disengage the threads 185 from those complementary threads formed within the blood collection port.

In an embodiment, the saline flush tube described herein, may also include a cap 135 as described in connection with FIGS. 3A, 3B, and 3C. In an embodiment, the threads formed on a cap of the saline flush tube may also include a locking mechanism that causes the saline flush tube to be locked into the blood collection port of the blood collection system so as to prevent any subsequent removal of the saline flush tube from the blood collection port. The locking mechanism may prevent the removal of the saline flush tube so as to prevent other blood collection tubes 130 from being placed into the blood collection port thereby preventing subsequent blood samples from entering the catheter after the saline flush.

FIG. 4 is a flow diagram illustrating an operation of a blood sample collection system 100 according to an embodiment of the present disclosure. Starting at a left-most image of the blood collection system 100, the blood collection system 100 has a baffle 120 placed in an expanded state as a result of the pressure within the baffle 120, baffle conduit 145 and baffle needle 160 being equal to atmosphere outside of the housing 105.

Moving to a next image of the blood collection system 100 to the right, a blood collection tube 130 has been introduced into the blood collection port 132 of the blood collection system 100. Upon the baffle needle 160 coming into atmospheric communication with the interior of the blood collection tube 130, at vacuum, the gases within the interior of the baffle 120 may be sucked into the interior of the blood collection tube 130. This results in a spring bias of the baffle spring 125 formed within the baffle 120 to be overcome and compression of the baffle spring 125 and baffle 120. At this point, all or nearly all of the gases within the baffle 120 may have been displaced into the interior of the blood collection tube 130 with the negative pressure within the blood collection tube 130 being reduced or eliminated in some examples.

Moving to a next image of the blood collection system 100 to the right, the blood collection system 100 has collected an amount of blood 195 within the blood collection tube 130. The collection of this amount of blood 195 into the blood collection tube 130 causes an amount of gases to be displaced within the blood collection tube 130 and passed into the interior of the baffle 120. As shown, the baffle 120 is shown to be in a semi-expanded state due to the spring 125 expanding the baffle 120 when the negative pressure placed on the interior of the baffle 120 is reduced. In an embodiment, the coupling of the blood collection tube 130 at the blood collection port 132 causes the total vacuum pressure within the blood collection tube 130 and baffle 120 to be reduced from 100 mmHg to 50 mmHg. Other different volumes within the blood collection tube 130 and baffle 120 may also be contemplated along with other levels of vacuum created within the blood collection tube 130. The examples of vacuum pressures (negative pressures) and volumes presented herein, therefore, are meant merely as an example, and the present specification contemplates these other volumes and pressures. In the embodiments presented herein, therefore, contemplates that the displacement of the gas within the baffle 120 either out of or into the blood collection tube 130 may vary depending on the volumes of the blood collection tube 130 and baffle 120 as well as the initial vacuum presented within the blood collection tube 130. This may or may not affect the timing of the displacement of the gases relative to the blood sample received at the blood collection tube 130.

Moving to the right-most image in FIG. 4, the blood collection tube 130 is shown to be full of the blood sample with the baffle 120 being fully expanded. The full expansion of baffle 120 may indicate to a clinician that the blood collection tube 130 is full and that the clinician may remove the blood collection tube 130 from the housing 105. As described herein, upon removal of the blood collection tube 130, a clinician may introduce a saline flush tube that pushes saline through the collection needle 150 and into an IV catheter coupled to the blood collection system 100.

The flow diagram shown in FIG. 4 may continue, in some embodiments, with introducing a new blood collection tube 130 at the blood collection port 132. The introduction of the new blood collection tube 130 allows for a clinician to retrieve another blood sample at the same blood collection system 100. This may be done as a result of the baffle needle 160 being decoupled from the previous blood collection tube 130 and being allowed to be exposed to atmosphere pressures present outside of the housing 105. In an embodiment, the baffle needle 160 may be shorter than the collection needle 150 so that the collection of blood 195 may not hinder the transfer of gases out of the blood collection tube 130 and into the baffle 120. In a specific embodiment, as the blood 195 level in the blood collection tube 130 rises and comes in contact with the baffle needle 160, the pressures within the blood collection tube 130 may prevent further accumulation of blood 195 within the blood collection tube 130. In this embodiment, the baffle 120 may remain in a less than fully expanded state until the blood collection tube 130 is removed thereby allowing gases to pass into the baffle 120 and the baffle spring 125 to be extended.

Figure 5:
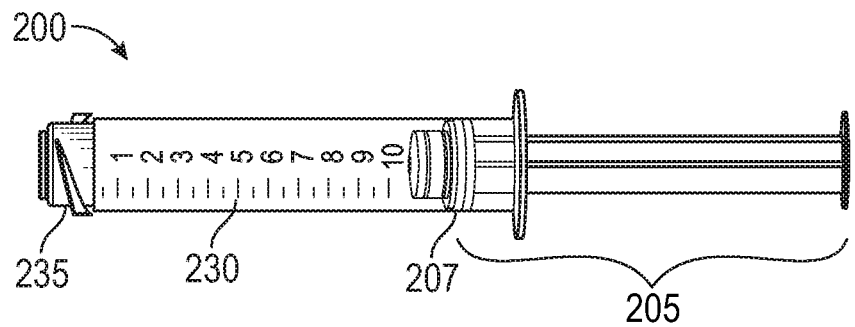
FIG. 5 is side view of a compressed saline flush tube according to an embodiment of the present disclosure.

FIG. 5 is side view of a compressed saline flush tube 200 according to an embodiment of the present disclosure. The saline flush tube 200 may be introduced at the blood collection port within the housing of the blood collection system as described herein. The saline flush tube 200 may be introduced at the blood collection port within the housing of the blood collection system so that a saline may be passed through the collection needle, hub lead, and hub and to an IV catheter fluidically coupled to the blood collection system described herein.

The saline flush tube 200 may include a cap 235, an internal volume 230 filled with saline, a plunger arm 205, and a plunger head 207 mechanically coupled to the plunger 205. These will be described in more detail.

The cap 235 may be any type of cap that may interface with the blood collection port of the blood collection system as described herein. In a specific embodiment, the cap 235 may include a number of threads and a rubber membrane similar to the cap described in connection with FIGS. 3A, 3B, and 3C. Upon insertion of the saline flush tube 200 into the blood collection tube, the rubber membrane may be pierced by the baffle needle and collection needle similar to the blood collection tube 130 described herein. This piercing creates two saline paths via the baffle needle and collection needle. However, in a specific embodiment, presented herein, as the saline comes in contact with the filter placed between the baffle needle and baffle conduit, the saline may interact with the filter causing the filter to seal up. In a specific embodiment, the saline may interact with a chemical placed on the filter that causes the filter to be gas permeable but seals the filter to the passage of any fluids such as the saline. In this example the chemical may be a crosslinked polyacrylamide.

With the filter rendered impermeable to the saline, the saline may be forced into the collection needle as the clinician applies a force to the plunger arm 205. The plunger arm 205 may cause the plunger head 207 to be moved towards the cap 235 such that the saline is pushed through the collection needle and into the IV catheter as described herein. The saline flush tube 200 is used to flush the IV catheter of any blood so that there is no coagulation of blood within the fluidic channels of the IV catheter.

In an embodiment, the threads formed on the cap 235 of the saline flush tube 200 may be formed to include a locking mechanism that prevents the saline flush tube 200 from being removed from the blood collection port. This locking mechanism may prevent the use or connection of any other blood collection tube at the blood collection port so that the IV catheter may remain flushed until another blood collection system 100 is fluidically coupled to the IV catheter for a subsequent or a subsequent series of blood draws.

Figure 6:
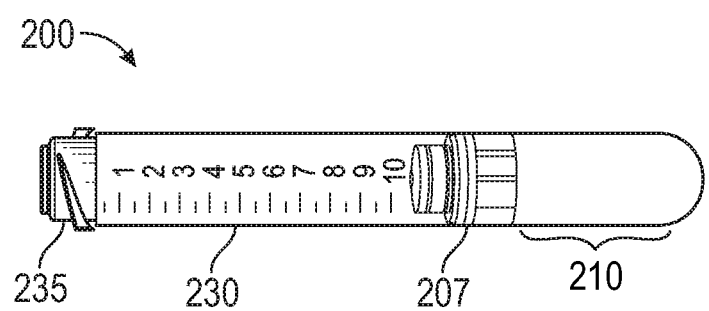
FIG. 6 is side view of a compressed saline flush tube according to an embodiment of the present disclosure.

FIG. 6 is side view of an air compressed saline flush tube 200 according to an embodiment of the present disclosure. The air compressed saline flush tube 200 may be introduced at the blood collection port within the housing of the blood collection system so that a saline may be passed through the collection needle, hub lead, and hub and to an IV catheter fluidically coupled to the blood collection system described herein.

The air compressed saline flush tube 200 may include a cap 235, an internal volume 230 of saline, a compressed air chamber 210, and a plunger head 207. These will be described in more detail.

The cap 235 may be any type of cap that may interface with the blood collection port of the blood collection system as described herein. In a specific embodiment, the cap 235 may include a number of threads and a rubber membrane similar to the cap described in connection with FIGS. 3A, 3B, and 3C. Upon insertion of the saline flush tube 200 into the blood collection tube, the rubber membrane may be pierced by the baffle needle and collection needle similar to the blood collection tube 130 described herein. This piercing creates two saline paths via the baffle needle and collection needle. However, in a specific embodiment, presented herein, as the saline comes in contact with the filter placed between the baffle needle and baffle conduit, the saline may interact with the filter causing the filter to seal up. In a specific embodiment, the saline may interact with a chemical placed on the filter that causes the filter to be gas permeable but seals the filter to the passage of any fluids such as the saline. In this example the chemical may be a crosslinked polyacrylamide.

With the filter rendered impermeable to the saline, the saline may be forced into the collection needle as the compressed air with the compressed air chamber 210 pushes against the plunger head 207. Unlike the use of a physical plunger arm as described in connection with FIG. 5, the compressed air within the compressed air chamber 210 automatically presses against the plunger head 207 and moves the plunger head 207 as saline is moved from the internal volume 230 and through the collection needle.

In an embodiment, the threads formed on the cap 235 of the air compressed saline flush tube 200 may be formed to include a locking mechanism that prevents the air compressed saline flush tube 200 from being removed from the blood collection port. This locking mechanism may prevent the use or connection of any other blood collection tube at the blood collection port so that the IV catheter may remain flushed until another blood collection system 100 is fluidically coupled to the IV catheter for a subsequent or a subsequent series of blood draws.

Figure 7:
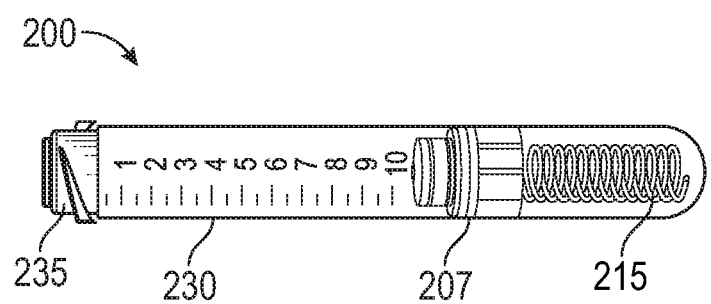
FIG. 7 is side view of a compressed saline flush tube according to an embodiment of the present disclosure.

FIG. 7 is side view of a spring compressed saline flush tube 200 according to an embodiment of the present disclosure. The spring compressed saline flush tube 200 may include a cap 235, an internal volume 230 of saline, a spring 215 formed within a spring chamber, and a plunger head 207 mechanically coupled to the spring 215. These will be described in more detail.

The cap 235 may be any type of cap that may interface with the blood collection port of the blood collection system as described herein. In a specific embodiment, the cap 235 may include a number of threads and a rubber membrane similar to the cap described in connection with FIGS. 3A, 3B, and 3C. Upon insertion of the spring compressed saline flush tube 200 into the blood collection tube, the rubber membrane may be pierced by the baffle needle and collection needle similar to the blood collection tube 130 described herein. This piercing creates two saline paths via the baffle needle and collection needle. However, in a specific embodiment, presented herein, as the saline comes in contact with the filter placed between the baffle needle and baffle conduit, the saline may interact with the filter causing the filter to seal up. In a specific embodiment, the saline may interact with a chemical placed on the filter that causes the filter to be gas permeable but seals the filter to the passage of any fluids such as the saline. In this example the chemical may be a crosslinked polyacrylamide.

With the filter rendered impermeable to the saline, the saline may be forced into the collection needle as the spring 215 pushes against the plunger head 207. Unlike the use of a physical plunger arm as described in connection with FIG. 5, the spring 215 within the spring chamber automatically presses against the plunger head 207 and moves the plunger head 207 as saline is moved from the internal volume 230 and through the collection needle.

In an embodiment, the threads formed on the cap 235 of the spring compressed saline flush tube 200 may be formed to include a locking mechanism that prevents the spring compressed saline flush tube 200 from being removed from the blood collection port. This locking mechanism may prevent the use or connection of any other blood collection tube at the blood collection port so that the IV catheter may remain flushed until another blood collection system 100 is fluidically coupled to the IV catheter for a subsequent or a subsequent series of blood draws.

Figure 8:
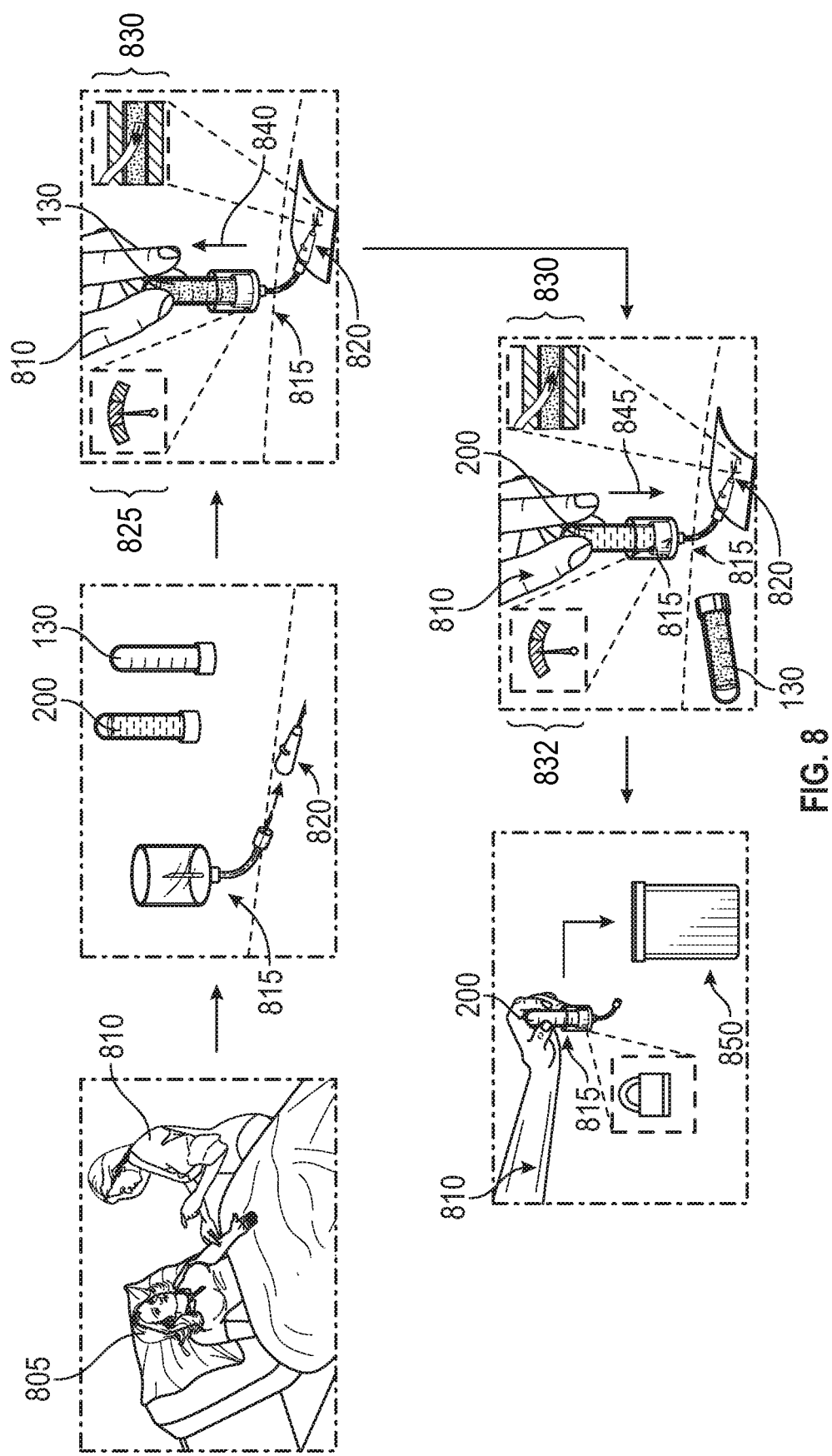
FIG. 8 is flow diagram illustrating a use of a blood collection system according to an embodiment of the present disclosure.

FIG. 8 is flow diagram illustrating a use of a blood collection system according to an embodiment of the present disclosure. The flow diagram shows a top, left-most panel with a clinician 810 addressing an IV insertion location on a patient 805. Once an appropriate location is identified, an IV catheter 820 may be inserted into the patient's 805 blood vessel as indicated in a top, center panel. At this point, the housing 815 of a blood collection system may be coupled to the IV catheter 820 using the hub of the housing 815 as described in connection with FIG. 1. During use, the clinician 810 is provided with a blood collection tube 130 and a saline flush tube 200. The blood collection tube 130 may be any blood collection tube described here and may include any volume of vacuumed space therein. The saline flush tube 200 may be any type of saline flush tube 200 described herein and specifically in connection with either of FIG. 5, 6, or 7.

The flow diagram further shows at a top, right-most panel, the introduction of the blood collection tube 130 at a blood collection port on the housing 815. In an embodiment, the catheter (shown in cut-out 830) is in fluid communication with a patient's blood vessel. As a result, the vacuum within the blood collection tube 130 may draw out 840 the blood within the blood vessel until a sufficient amount of blood is received into the blood collection tube 130.

In some embodiments, the housing 815 may further include a baffle chamber and baffle as described herein. In this embodiment, the baffle may be used to counteract, to some level, the forces exerted on the blood as the blood is drawn out of 840 the patient's 805 blood vessel as described herein.

In an embodiment, the blood collection tube 130 or housing 815 may further include a hemolysis indicator 825 (shown in cutout). In this embodiment, the hemolysis indicator 825 may provide an indication as to the types of pressures exerted on the blood being drawn 840 into the blood collection tube 130. In this embodiment, the hemolysis indicator 825 may be atmospherically coupled to a pressure gauge such that the pressure gauge indicates whether a threshold pressure is exerted onto the blood and therefore, potentially, ruins the blood sample being drawn 840. In another embodiment, the hemolysis indicator 825 may regulate the pressure and flow of the blood such that the hemolysis indicator 825 ensures sample quality and reducing the potential of hemolysis and vessel collapse.

The flow diagram may continue, at the bottom, right-most panel, with the application of the saline flush tube 200 at the housing 815. In this embodiment, the saline flush tube 200 may flush 845 a saline through the IV catheter 820 and into the blood stream of the patient 805 so that the IV catheter 820 may be cleared for subsequent injections or blood draws.

In an embodiment, the housing 815 may also include a flush rate indicator 832. The flush rate indicator 832 may indicate to a clinician 810 the rate at which the saline is being flushed 845 into the patient's 805 blood stream. If, for example, the flushing 845 is too rapid, the indicator may so indicate telling the clinician 810 that damage may occur to the patient 805 or parts of the blood collection system. In an embodiment, the flush rate indicator 832 may also or alternatively act as a flush rate controller that controls the flow of the saline as it enters the patient's body.

A bottom, left most panel of the flow diagram shows the removal of the blood collection system from the IV catheter 820 and the disposal of the blood collection system. As indicated the blood collection system may still have the saline flush tube 200 coupled thereto. In this embodiment, a cap of the saline flush tube 200 may have threads that permanently interlock with matching threads formed in on internal surface of the blood collection port. By locking the saline flush tube 200 into the blood collection system, the clinician 810 is prevented from conducted a subsequent blood draw and potentially not having a saline flush tube 200 available to conduct a subsequent flushing 845.

Figure 9:
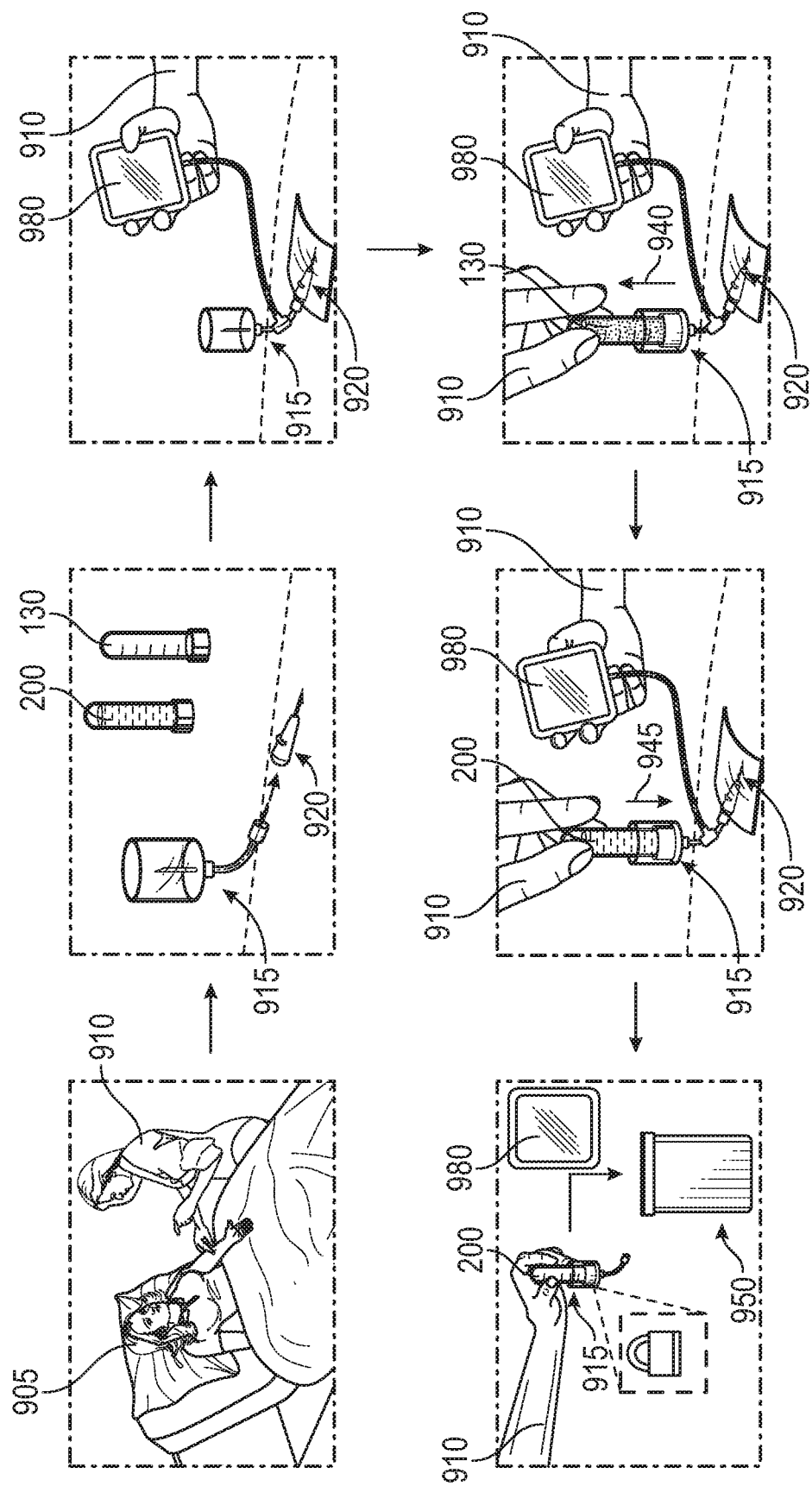
FIG. 9 is flow diagram illustrating a use of a blood collection system according to an embodiment of the present disclosure.

FIG. 9 is flow diagram illustrating a use of a blood collection system according to an embodiment of the present disclosure. The flow diagram shows a top, left-most panel with a clinician 910 addressing an IV insertion location on a patient 905. Once an appropriate location is identified, an IV catheter 920 may be inserted into the patient's 905 blood vessel as indicated in a top, center panel. At this point, the housing 915 of a blood collection system may be coupled to the IV catheter 920 using the hub of the housing 915 as described in connection with FIG. 1. During use, the clinician 910 is provided with a blood collection tube 130 and a saline flush tube 200. The blood collection tube 130 may be any blood collection tube described here and may include any volume of vacuumed space therein. The saline flush tube 200 may be any type of saline flush tube 200 described herein and specifically in connection with either of FIG. 5, 6, or 7.

The flow diagram further shows at a top, right-most panel, the coupling of a blood draw monitor 980 between the IV catheter 920 and the housing 915. In this embodiment, the blood draw monitor 980 may monitor for the passage of fluids such as blood and saline as the clinician 810 conducts the blood draw. In an embodiment, the blood draw monitor 980 may assess and notify the clinician 910 when it is appropriate to collect blood samples. In this embodiment, the blood draw monitor 980 may assess specifically the blood and/or infusate dilution at a distal end of the IV catheter 920 needle and blood availability in the blood vessel.

The flow diagram shows, at the bottom, right-most panel, the introduction of the blood collection tube 130 at a blood collection port on the housing 915. In an embodiment, the blood draw monitor 980 is monitoring the blood drawn 940 and specifically the rate of the blood draw. This is done as the vacuum within the blood collection tube 130 draws 940 the blood within the blood vessel until a sufficient amount of blood is received into the blood collection tube 130.

In some embodiments, the housing 915 may further include a baffle chamber and baffle as described herein. In this embodiment, the baffle may be used to counteract, to some level, the forces exerted on the blood as the blood is drawn out of 940 the patient's 905 blood vessel as described herein.

In these embodiments, the blood draw monitor 980 may provide an indication as to the types of pressures exerted on the blood being drawn 940 into the blood collection tube 130. In this embodiment, the blood draw monitor 980 may be atmospherically coupled to a pressure gauge such that the pressure gauge indicates whether a threshold pressure is exerted onto the blood and therefore, potentially, ruins the blood sample being drawn 940.

The flow diagram may continue, at the bottom, center panel, with the application of the saline flush tube 200 at the housing 915. In this embodiment, the saline flush tube 200 may flush 945 a saline through the IV catheter 920 and into the blood stream of the patient 905 so that the IV catheter 920 may be cleared for subsequent injections or blood draws.

In an embodiment, the blood draw monitor 980 may indicate to a clinician 910 the rate at which the saline is being flushed 945 into the patient's 905 blood stream. If, for example, the flushing 945 is too rapid, the blood draw monitor 980 may so indicate telling the clinician 910 that damage may occur to the patient 905 or parts of the blood collection system. In an embodiment, the blood draw monitor 980 may additionally or alternatively assess whether the IV catheter 920 was sufficiently flushed. In this embodiment, certain fluidic sensors may be employed to determine, for example, a saline to blood cell dilution rate among other fluidic qualities.

A bottom, left most panel of the flow diagram shows the removal of the blood collection system from the IV catheter 920 and the disposal of the blood collection system. As indicated the blood collection system may still have the saline flush tube 200 coupled thereto. In this embodiment, a cap of the saline flush tube 200 may have threads that permanently interlock with matching threads formed in on internal surface of the blood collection port. By locking the saline flush tube 200 into the blood collection system, the clinician 810 is prevented from conducted a subsequent blood draw and potentially not having a saline flush tube 200 available to conduct a subsequent flushing 945.

Figure 10:
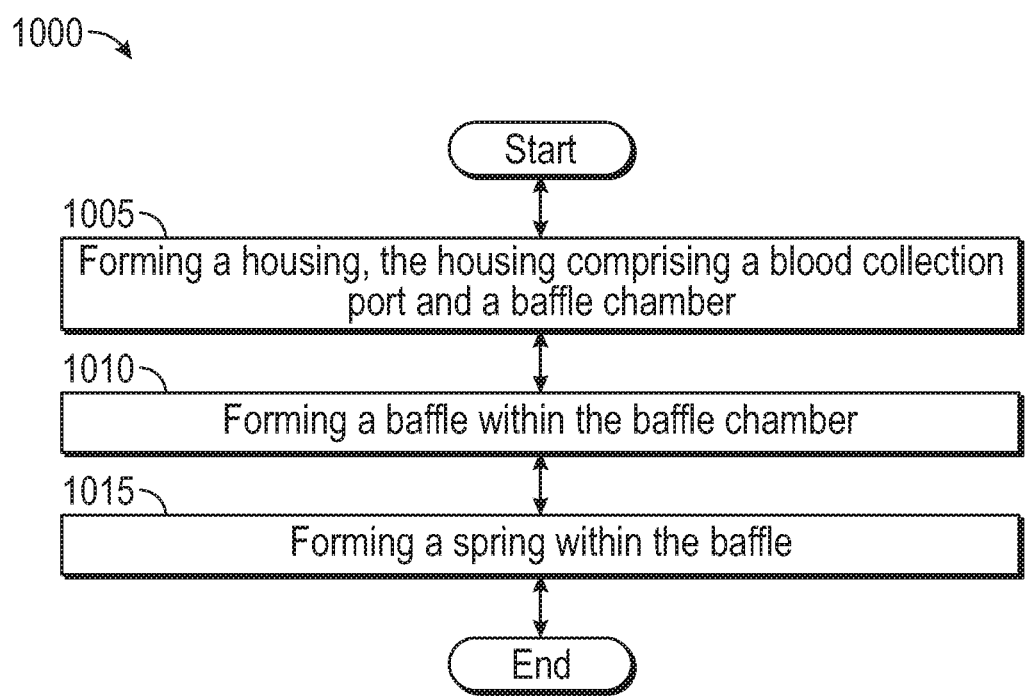
FIG. 10 is a flowchart depicting a method of manufacturing a blood sample collection system according to some embodiments of the present disclosure.

FIG. 10 is a flowchart depicting a method 1000 of manufacturing a blood sample collection system according to some embodiments of the present disclosure. The method 1000 may include, at block 1005, forming a housing, the housing comprising a blood collection port and a baffle chamber. As descried herein, the baffle may be atmospherically coupled to the collection port via a baffle conduit and a baffle needle. The baffle conduit may be formed through the housing in an embodiment, or may be formed out of a tube. In either example, the interior of the baffle is atmospherically coupled to a distal end of the baffle needle.

The blood collection portion may include the previously-described baffle needle as well as a collection needle. The collection needle may be fluidically coupled to a hub or other connection device that leads to an IV catheter placed within a patient's blood vessel.

The method 1000 may, at block 1010, further include forming a baffle within the baffle chamber. As described, an interior space formed within the baffle may be atmospherically coupled to the baffle needle. This allows the baffle to maintain an amount of gas therein for use during a blood draw process described herein.

The method 1000 may further include forming a spring within the baffle at block 1015. As described herein, the spring is biased so as to cause the baffle to be fully inflated unless certain negative pressures are applied to the interior of the baffle. This negative pressure may result from a clinician coupling a vacutainer-type blood collection tube to the baffle needle. Because of the vacuum formed in the vacutainer-type blood collection tube, the gases within the baffle may be displaced into the vacutainer-type blood collection tube until blood is introduced into the vacutainer-type blood collection tube. As blood is pulled into the vacutainer-type blood collection tube via the remaining vacuum pressure in the vacutainer-type blood collection tube, gases are displaced once again into the baffle commensurate with the changing level of blood within the vacutainer-type blood collection tube.

Again, it is understood that the embodiments of the present application may be combined. As an example, the embodiments of FIGS. 1-10 may be arranged to fit specific uses based on the type of action being conducted.

The presently described blood sample collection system may allow for the collection of a blood sample without creating hemolysis resulting from the use of the baffle. The blood sample collection system may also be selectively removed from an IV catheter and also allow for the application of a saline flush without uncoupling the blood sample collection system and coupling an IV flush. This reduces the amount of interaction at the IV catheter by a clinician thereby maintaining the position of the IV catheter.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. A blood sample collection system, comprising:
   a housing, the housing comprising:
     a blood collection port; and
     a baffle chamber;
   a collection needle formed through the housing and into the blood collection port;
   a baffle formed within the baffle chamber to counteract a vacuum within a blood collection tube when pierced by the needle; and
   a spring disposed within the baffle and biased such that the baffle is in an expanded state.

2. The blood sample collection system of claim 1, further comprising a baffle needle formed through the housing and fluidically coupling the baffle with an interior of the blood collection tube.

3. The blood sample collection system of claim 2, further comprising a baffle conduit formed in the housing to fluidically couple the baffle to the baffle needle.

4. The blood sample collection system of claim 3, further comprising a filter formed in the baffle conduit to prevent blood from entering the baffle.

5. The blood sample collection system of claim 1, wherein the blood collection port comprises a thread to receive a complimentary thread formed on a blood collection tube.

6. The blood sample collection system of claim 1, further comprising a hub connector fluidically coupled to the needle to fluidically couple the blood sample collection system to an intravenous device.

7. The blood sample collection system of claim 1, wherein the baffle has an internal volume of 5 ml.

8. The blood sample collection system of claim 1, further comprising the blood collection tube, wherein the blood collection tube includes a thread to engage a surface within the blood collection port.

9. The blood sample collection system of claim 1, further comprising a compressed saline flush tube to be received at the blood collection port and replace the blood collection tube subsequent to a blood collection process.

10. The blood sample collection system of claim 9, wherein the compressed saline flush tube comprises a locking thread that, once introduced into the blood collection port, locks the compressed saline flush tube into the blood collection port to prevent removal of the compressed saline flush tube.

11. A peripheral intravenous catheter (PIVC) device, comprising:
a housing, the housing comprising:
   a blood collection port, the blood collection port comprising a thread to receive a complementary thread from a blood collection tube placed in the blood collection port; and
   a baffle chamber fluidically coupled to the blood collection port via a baffle conduit formed into the housing;
a needle formed through the housing and into the blood collection port;
a baffle formed within the baffle chamber to counteract a vacuum within a blood collection tube when pierced by the needle; and
a spring disposed within the baffle and biased such that the baffle is in an expanded state.

12. The PIVC device of claim 11, further comprising a baffle needle formed through the housing and fluidically coupling the baffle with the interior of the blood collection tube via the baffle conduit.

* * * * *